(12) United States Patent
Leander et al.

(10) Patent No.: US 6,440,428 B1
(45) Date of Patent: *Aug. 27, 2002

(54) PODOPHYLLOTOXIN PREPARATION CONTAINING TRIGLYCERIDES

(75) Inventors: Kurt Leander, Peseux; Jan Gunzinger, Couvet, both of (CH); Börje Rosen, Vallentuna (SE)

(73) Assignee: Analytecon SA, Couvet (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/127,121

(22) Filed: Sep. 27, 1993

Related U.S. Application Data

(63) Continuation of application No. 07/778,920, filed on Mar. 2, 1992, now abandoned.

(30) Foreign Application Priority Data

Jul. 31, 1989 (SE) .............................. 8902624-9
Jul. 17, 1990 (WO) ............................... PCT/SE90/00492

(51) Int. Cl.⁷ ........................... A61K 7/00; A61K 47/00
(52) U.S. Cl. ........................ 424/401; 514/784; 514/785; 514/786; 514/863; 514/943; 514/969
(58) Field of Search .......................... 424/401; 514/969, 514/784, 785, 786, 943, 863

(56) References Cited

U.S. PATENT DOCUMENTS

| | | | | |
|---|---|---|---|---|
| 3,826,845 A | | 7/1974 | Suyama et al. ............. 424/365 |
| 4,235,889 A | * | 11/1980 | Evers ......................... 514/863 |
| 4,341,783 A | * | 7/1982 | Scheindlin ................. 514/863 |
| 4,699,929 A | | 10/1987 | Mustakallio et al. ....... 514/680 |
| 4,746,675 A | * | 5/1988 | Makino ...................... 514/947 |
| 4,751,075 A | * | 6/1988 | Chernowsky ............... 514/969 |
| 4,769,390 A | * | 9/1988 | Roelz ......................... 514/863 |
| 4,788,216 A | | 11/1988 | Leander et al. ............. 514/468 |
| 4,789,667 A | * | 12/1988 | Makino ...................... 514/161 |
| 4,837,019 A | * | 6/1989 | Georgalas ................... 424/101 |
| 4,863,970 A | * | 9/1989 | Patel .......................... 514/785 |
| 4,895,727 A | | 1/1990 | Allen ......................... 424/462 |
| 4,994,496 A | * | 2/1991 | Repasky ..................... 514/775 |
| 5,104,656 A | * | 4/1992 | Seth ........................... 424/401 |

FOREIGN PATENT DOCUMENTS

| | | |
|---|---|---|
| EP | 0119852 | 9/1984 |
| GB | 1278902 | 6/1972 |
| GB | 1370699 | 10/1974 |
| WO | WO 86/06586 | 11/1986 |

OTHER PUBLICATIONS

Cosmetic and Toiletry Formulations, Second Edition, vol. 2 (Noyes Publication, 1992) pp. 211, 248, 291, 293, 313, 321, 323, 330, 333.*

\* cited by examiner

Primary Examiner—Thurman K. Page
Assistant Examiner—Brian K. Seidleck
(74) Attorney, Agent, or Firm—Birch, Stewart, Kolasch & Birch, LLP

(57) ABSTRACT

The invention refers to new pharmaceutical preparations for the treatment of psoriasis and condyloma acuminata, and containing podophyllotoxin in combination with a liquid triglyceride.

12 Claims, No Drawings

PODOPHYLLOTOXIN PREPARATION CONTAINING TRIGLYCERIDES

This application is a continuation of application Ser. No. 07/778,920 filed on Mar. 2, 1992, now abandoned.

FIELD OF THE INVENTION

The present invention relates to new pharmaceutical preparations, primarily in the form av creams, which contain podophyllotoxin as the active ingredient, for the treatment of psoriasis and condyloma acuminata. The invention also refers to the use of such preparations for the manufacture of creams for the treatment of psoriasis and condyloma acuminata.

BACKGROUND OF THE INVENTION

From EP-B1-119 852, preparations of podophyllotoxin for the treatment of condyloma acuminata are known. These preparations comprise podophyllotoxin and at least one glycol selected from alkylene glycols and polyalkylene glycols.

Furthermore, U.S. Pat. No. 4,788,216 describes a method of treating psoriasis, wherein podophyllotoxin is administered. It is mentioned that a cream can be used, but no specific pharmaceutical preparation is described.

There is a desire for improvement in the existing preparations of podophyllotoxin, as regards the effect and the stability. These improvements are achieved through the present invention.

DESCRIPTION OF THE INVENTION

It is the object of the invention to provide preparations for the treatment of psoriasis and condyloma acuminata, having a good clinical effect and good stability.

According to the invention, it has now unexpectedly been found that a composition of podophyllotoxin with one or more liquid triglycerides gives a stable preparation which shows a good effect against psoriasis and condyloma acuminata, with few side effects. Preferably the preparation is in the form of a cream or ointment, wherein the triglycerides are emulsified together with an aqueous phase.

For the treatment of psoriasis, the preparation should contain between 0.02 and 1 weight percent of podophyllotoxin, and preferably then between 0.05 and 0.5 weight percent. It is especially preferred that the preparation contains about 0.1 weight percent. As the treatment of psoriasis is usually carried out during long periods of time, it is important that the concentration of podophyllotoxin can be kept low in order to avoid unwanted side effects.

In the present specification and claims, all percentages, unless stated otherwise, are calculated as weight percent of the total preparation.

For the treatment of condyloma acuminata, the preparation should contain between 0.01 and 1 weight percent of podophyllotoxin, and preferably then between 0.15 and 0.5 weight percent. A preparation containing about 0.3 weight percent is especially preferred.

The preparations usually contain between 3 and 15 weight percent of the liquid triglyceride or triglycerides, and preferably then about 10 weight percent. The liquid triglyceride preferably is of medium chain length, containing 6 to 14 carbon atoms per chain, and most preferably it consists of a triglyceride of caprylic/capric acid (fractionated coconut oil). One type of such fractionated coconut oil is sold under the trade name Miglyol.

In addition to the podophyllotoxin and the liquid triglyceride or triglycerides, the preparations also contain water in an amount from about 50 to about 85 weight percent, and auxiliary substances, such as emulsifiers, spreading agents, preserving agents, antioxidants and buffers to maintain the pH value at a given level. The preparation for the treatment of psoriasis may also contain a glycol or polyol.

As suitable emulsifiers may be mentioned the products sold under the trade names "Emulsifier E 2155" (polyethylene glycol(7) stearyl ether+polyethylene glycol (10) stearyl ether+stearyl alcohol), "Brij 72" (polyethylene glycol(2) stearyl ether), "Brij 721" (polyethylene glycol(21) stearyl ether), "Arlatone 983 S" (polyethylene glycol(5) glyceryl stearate) and "Arlacel 582" (polyethylene glycol-glycerol-sorbitan isostearate). This list is not exhaustive, and other non-ionic emulsifiers having similar HLB (hydrophilic-lipophilic balance) values may also be used. The emulsifier is used in an amount sufficient to attain the desired emulsifying effect. This amount can easily be determined by a person skilled in the emulsifying art by simple routine tests. Usually, an amount from about 3 to about 10 weight percent is used, depending on the specific emulsifying system used, but these values are not critical.

Spreading agents assist in the spreading out of the preparation when it is applied to the skin or mucous membranes. As one known such agent may be mentioned isopropyl myristate, but other agents are also known to those skilled in the art. The spreading agent may be used in an amount of up to about 5 weight percent.

Preserving agents and antioxidants are used to stabilize the preparation against harmful external influences, such as microorganisms and oxygen. As suitable preserving agents may be mentioned methylparaben (methyl 4-hydroxybenzoate), propylparaben (propyl 4-hydroxybenzoate) and sorbic acid. The preserving agents are conventionally used in amounts up to about 0.5 weight percent, and usually then in amounts up to about 0.2 weight percent. As an example of a suitable antioxidant can be mentioned t-butylhydroxyanisole, t-butylhydroxytoluene, and ascorbic acid and its derivatives, such as ascorbyl palmitate, but other suitable antioxidants are well-known to those skilled in the art. The antioxidant is used in a very small amount, usually up to about 0.2 weight percent.

To stabilize the podophyllotoxin against chemical alteration, the preparation should have a pH value on the acid side, usually then between 2 and 6, and preferably between 2.6 and 3.5. This is achieved by the addition of a suitable acid or acid buffer, such as phosphoric acid. Other suitable acids or acid buffers are well-known to those skilled in the art, and it goes without saying that the acid or acid buffer used must be pharmaceutically acceptable. The acid or acid buffer is added in an amount which gives the desired pH value in the finished preparation.

Other additives which are well-known and used in the art may also be included in the preparation.

The preparations are intended to be administered topically to the lesions of a patient suffering from psoriasis. In the case of condyloma acuminata, the preparations are intended for topical, vaginal and anal use. The amount to be applied and the frequency of applications is determined by the physician on the basis of such factors as the age and health status of the patient, the severity of the affliction, and others.

In clinical tests, the pharmaceutical preparations of the invention have been found to have an advantageous activity with minimal or no adverse reactions.

For men and women suffering from condyloma acuminata, most patients have been completely clear after only a few weeks of topical treatment. In addition, the number of treatment periods have been reduced with creams in accordance to the invention. In comparison with placebo, the difference is statistically significant ($p=<0.05$).

In the treatment of psoriasis, patients with symptoms like desquamation and induration have been highly improved in a few weeks by a topical application twice daily. Each patient has been treated on a specific lesioned area, while other untreated areas served as control. The cream of the invention showed a superior effect in comparison with placebo after only four weeks of treatment. This effect is statistically significant ($p=<0.05$).

In both cases, only a minimum of adverse reactions were observed.

The invention is further illustrated by the following examples of a number of preparations in accordance with the invention. These examples are in no way intended to restrict the scope of the invention.

In the preparation of the following creams, the aqueous phase and the fatty phase are each separately mixed and heated. The aqueous phase is then added to the fatty phase, followed by the addition of the active ingredient suspended in the liquid triglyceride or triglycerides. The mixture is then homogenized, stirred and cooled to give the desired cream.

EXAMPLE 1

Cream for the treatment of condyloma acuminata

|  | grams |
|---|---|
| Fatty phase | |
| Emulgator E-2155 | 8 |
| Hexadecanol | 2 |
| Octadecanol | 2 |
| Isopropyl myristate | 2 |
| Liquid paraffin | 3 |
| Fractionated coconut oil | 10 |
| Butylhydroxyanisole | 0.008 |
| Aqueous phase | |
| Water | 72.34 |
| Methylparaben | 0.10 |
| Propylparaben | 0.03 |
| Phosphoric acid 1 M | 0.1 |
| Sorbic acid | 0.12 |
| Active ingredient | |
| Podophyllotoxin | 0.3 |

EXAMPLE 2

Cream for the treatment of psoriasis

|  | grams |
|---|---|
| Fatty phase | |
| Protegin WX | 22 |
| Fractionated coconut oil | 10 |
| Isopropyl myristate | 3 |
| Aqueous phase | |
| Water | 59.05 |
| Methylparaben | 0.10 |
| Propylparaben | 0.03 |

-continued

|  | grams |
|---|---|
| Propylene glycol | 5 |
| Phosphoric acid 1 M | 0.1 |
| Magnesium sulfate × 7 $H_2O$ | 0.5 |
| Sorbic acid | 0.12 |
| Active ingredient | |
| Podophyllotoxin | 0.1 |

Protegin WX is an emulsifying preparation for creams, consisting of a mixture of petrolatum, ozokerite, hydrogenated castor oil, glyceryl oleate, polyglyceryl(4) isostearate and t-butylhydroxytoluene.

EXAMPLE 3

|  | grams |
|---|---|
| Fatty phase | |
| Emulsifier E-2155 | 8 |
| Hexadecanol | 2 |
| Octadecanol | 2 |
| Fractionated coconut oil | 15 |
| Liquid paraffin | 2 |
| Butylhydroxyanisole | 0.008 |
| Aqueous phase | |
| Water | 69.64 |
| Methylparaben | 0.10 |
| Propylparaben | 0.03 |
| Phosphoric acid 1 M | 0.1 |
| Sorbic acid | 0.12 |
| Active ingredient | |
| Podophyllotoxin | 1 |

EXAMPLE 4

|  | grams |
|---|---|
| Fatty phase | |
| Brij 72 | 3 |
| Brij 721 | 2 |
| Hexadecanol | 2 |
| Stearic acid | 1.5 |
| Fractionated coconut oil | 9 |
| Butylhydroxyanisole | 0.008 |
| Aqueous phase | |
| Water | 81.64 |
| Methylparaben | 0.10 |
| Propylparaben | 0.03 |
| Phosphoric acid 1 M | 0.1 |
| Sorbic acid | 0.12 |
| Active Ingredient | |
| Podophyllotoxin | 0.5 |

EXAMPLE 5

Cream for the treatment of condyloma acuminata

|  | grams |
|---|---|
| Fatty phase | |
| Arlatone 983 S | 5 |
| Hexadecanol | 2 |
| Stearic acid | 1.5 |
| Fractionated coconut oil | 3 |
| Liquid paraffin | 2 |
| Butylhydroxyanisole | 0.008 |
| Aqueous phase | |
| Water | 82.10 |
| Methylparaben | 0.10 |
| Propylparaben | 0.03 |
| Phosphoric acid 1 M | 0.1 |
| Propylene glycol | 4 |
| Sorbic acid | 0.12 |
| Active Ingredient | |
| Podophyllotoxin | 0.04 |

EXAMPLE 6

|  | grams |
|---|---|
| Fatty phase | |
| Arlacel 582 | 10 |
| Isopropyl myristate | 3 |
| Liquid paraffin | 10 |
| Fractionated coconut oil | 12 |
| Butylhydroxyanisole | 0.008 |
| Aqueous phase | |
| Water | 59.89 |
| Propylene glycol | 4 |
| MgSO$_4$ · 7H$_2$O | 0.5 |
| Phosphoric acid 1 M | 0.1 |
| Methylparaben | 0.10 |
| Propylparaben | 0.03 |
| Sorbic acid | 0.12 |
| Active Ingredient | |
| Podophyllotoxin | 0.25 |

What is claimed is:

1. A cream for the treatment of condyloma acuminata which comprises:
   a fatty phase containing 8 parts by weight of polyethylene glycol (7) stearyl ether, polyethylene glycol (10) stearyl ether and stearyl alcohol, 2 parts by weight hexadecanol, 2 parts by weight octadecanol, 2 parts by weight isopropyl myristate, 3 parts by weight liquid paraffin, 10 parts by weight fractionated coconut oil, and 0.008 parts by weight butylhydroxyanisole;
   an aqueous phase containing 71.642–72.632 parts by weight water, 0.10 parts by weight methylparaben, 0.03 parts by weight propylparaben, 0.1 parts by weight 1M phosphoric acid, and 0.12 parts by weight sorbic acid; and
   0.01–1 parts by weight podophyllotoxin as active ingredient.

2. A cream for the treatment of psoriasis which comprises:
   a fatty phase containing 22 parts by weight of petrolatum, ozokerite, hydrogenated castor oil, glyceryl oleate, polyglyceryl (4) isostearate and t-butylhydroxytoluene, 10 parts by weight fractionated coconut oil, and 3 parts by weight isopropyl myristate;
   an aqueous phase containing 58.15–59.13 parts by weight water, 0.10 parts by weight methylparaben, 0.03 parts by weight propylparaben, 5 parts by weight propylene glycol, 0.1 parts by weight 1M phosphoric acid, 0.5 parts by weight MgSO$_4$×7 H$_2$O, and 0.12 parts by weight sorbic acid; and 0.02–1 parts by weight podophyllotoxin as active ingredient.

3. A cream for the treatment of condyloma acuminata or psoriasis which comprises:
   a fatty phase containing 8 parts by weight of polyethylene glycol (7) stearyl ether, polyethylene glycol (10) stearyl ether and stearyl alcohol, 2 parts by weight hexadecanol, 2 parts by weight octadecanol, 15 parts by weight fractionated coconut oil, 2 parts by weight liquid paraffin, and 0.008 parts by weight butylhydroxyanisole;
   an aqueous phase containing 69.642–70.622 parts by weight water, 0.10 parts by weight methylparaben, 0.03 parts by weight propylparaben, 0.1 parts by weight 1M phosphoric acid, and 0.12 parts by weight sorbic acid; and
   0.02–1 part by weight podophyllotoxin as active ingredient.

4. A cream for the treatment of condyloma acuminata or psoriasis which comprises:
   a fatty phase containing 3 parts by weight polyethylene glycol (2) stearyl ether, 2 parts by weight polyethylene glycol (21) stearyl ether, 2 parts by weight hexadecanol, 1.5 parts by weight stearic acid, 9 parts by weight fractionated coconut oil, and 0.008 parts by weight butylhydroxyanisole;
   an aqueous phase containing 81.142–82.122 parts by weight water, 0.10 parts by weight methylparaben, 0.03 parts by weight propylparaben, 0.1 parts by weight 1M phosphoric acid, and 0.12 parts by weight sorbic acid; and
   0.02–1 parts by weight podophyllotoxin as active ingredient.

5. A cream for the treatment of condyloma acuminata which comprises:
   a fatty phase containing 5 parts by weight polyethylene glycol (5) glyceryl stearate, 2 parts by weight hexadecanol, 1.5 parts by weight stearic acid, 3 parts by weight fractionated coconut oil, 2 parts by weight liquid paraffin, and 0.008 parts by weight butylhydroxyanisole;
   an aqueous phase containing 81.142–82.132 parts by weight water, 0.10 parts by weight methylparaben, 0.03 parts by weight propylparaben, 0.1 parts by weight 1M phosphoric acid, 4 parts by weight propylene glycol, and 0.12 parts by weight sorbic acid; and
   0.01–1 parts by weight podophyllotoxin as active ingredient.

6. A cream for the treatment of condyloma acuminata or psoriasis which comprises:
   a fatty phase containing 10 parts by weight polyethylene glycol-glycerol-sorbitan isostearate, 3 parts by weight isopropyl myristate, 10 parts by weight liquid paraffin, 12 parts by weight fractionated coconut oil, and 0.008 parts by weight butylhydroxyanisole;
   an aqueous phase containing 59.142–60.122 parts by weight water, 4 parts by weight propylene glycol, 0.5 parts by weight MgSO$_4$×7 H$_2$O, 0.1 parts by weight 1M phosphoric acid, 0.10 parts by weight methylparaben, 0.03 parts by weight propylparaben, and 0.12 parts by weight sorbic acid; and 0.02–1 parts by weight podophyllotoxin as active ingredient.

7. The cream according to claim 1, wherein the podophyllotoxin is present in 0.15–0.5 parts by weight.

8. The cream according to claim 2, wherein the podophyllotoxin is present in 0.05–0.5 parts by weight.

9. The cream according to claim 3, wherein the podophyllotoxin is present in 0.05–0.5 parts by weight.

10. The cream according to claim 4, wherein the podophyllotoxin is present in 0.05–0.5 parts by weight.

11. The cream according to claim 5, wherein the podophyllotoxin is present in 0.04 parts by weight.

12. The cream according to claim 6, wherein the podophyllotoxin is present in 0.25 parts by weight.

* * * * *